United States Patent
Cho et al.

(10) Patent No.: US 6,506,601 B2
(45) Date of Patent: Jan. 14, 2003

(54) COMPOSITION AND METHOD FOR MEASURING THE FOLIAR UPTAKE OF PESTICIDES

(75) Inventors: Kwang-Yun Cho, Daejeon (KR); Ju-Hyun Yu, Daejeon (KR); He-Kyoung Lim, Daejeon (JP); Gyung-Ja Choi, Daejeon (JP); Jeong-Han Kim, Seoul (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 09/753,777

(22) Filed: Jan. 3, 2001

(65) Prior Publication Data

US 2001/0001713 A1 May 24, 2001

Related U.S. Application Data

(63) Continuation of application No. PCT/KR99/00342, filed on Jun. 29, 1999, now abandoned.

(30) Foreign Application Priority Data

May 10, 1999 (KR) ............................................. 99-16642

(51) Int. Cl.$^7$ ................................................. C12N 5/00
(52) U.S. Cl. ....................... 435/410; 504/116.1; 47/58.1
(58) Field of Search ....................... 435/410; 504/116.1; 47/58.1

(56) References Cited

U.S. PATENT DOCUMENTS 5,512,488 A * 4/1996 Eberendu et al.
5,872,091 A * 2/1999 Cuperus et al.

\* cited by examiner

*Primary Examiner*—Leon B. Lankford, Jr.
(74) *Attorney, Agent, or Firm*—Katten Muchin Zavis Rosenman

(57) ABSTRACT

A composition for measuring the foliar uptake of a pesticide comprising the pesticide and Congo Red as a tracer is disclosed together with a method for measuring the foliar uptake of a pesticide comprising the steps of (a) applying a composition containing the pesticide and Congo Red as a tracer to a plant and a control plate, (b) washing the plant and the control plate with a solvent to extract the pesticide and Congo Red, (c) measuring the concentrations of the pesticide and Congo Red in the wash extracts, and (d) calculating the foliar uptake of the pesticide.

10 Claims, No Drawings

COMPOSITION AND METHOD FOR MEASURING THE FOLIAR UPTAKE OF PESTICIDES

CROSS REFERENCE TO RELATED APPLICATION

This application is a continuation of International Application No. PCT/KR 99/00342, with an international filing date of Jun. 29, 1999, which designated the U.S. and is now abandoned.

FIELD OF THE INVENTION

The present invention relates to a composition and method for measuring the foliar uptake of an agrochemical. More specifically, it pertains to a composition for measuring the foliar uptake of an agrochemical comprising said agrochemical and Congo Red as a tracer; and a method for measuring the foliar uptake of an agrochemical using same.

BACKGROUND OF THE INVENTION

Hundreds of agrochemicals have been developed and used commercially to protect crops from weeds, pathogens and insects. However, the prolonged use of agrochemicals have induced the appearance of species which are resistant to once effective agrochemicals, and in order to control such resistant weeds, pathogens or insects, ever increasing amounts of agrochemicals have been applied, causing a serious environmental issue as well as a cost problem. Accordingly, besides the need to develop new classes of environmentally friendly agrochemicals, it is required to suppress the application rates of existing agrochemicals by way of improving, for instance, delivery systems through the addition of effective adjuvants thereto.

Examples of adjuvants used to enhance the activity of an agrochemical include a spreader or spreader-sticker which facilitates the adherence of an agrochemical to a subject crop, a rainfasting agent for preventing the loss of an agrochemical due to rainwash, and a penetrant which allows the absorption of a larger than normal amount of an agrochemical by a subject crop.

As a larger amount of an agrochemical is absorbed by plant tissues in a short time, the manifestation of the intended effect of the agrochemical becomes faster and stronger, as in case of a herbicide. In case of a fungicide, its protective and curative effects against a pathogenic disease increase when a suitable penetrant is employed. Further, in case a proper penetrant is added to a pesticide, it is possible to obtain a superior pesticidal effect of killing harmful insects at sites where the pesticide was not directly applied.

For example, B. Terence et al. have reported that dimethomorph, which is used for treating vine plants infected by downy mildew, potato late blight and pepper blight, showed significantly higher curative activity when used in combination with a nonionic surfactant, e.g., lauryl alcohol ethoxylates(*Pesticide Science*, 46, 199–213 & 355–359(1996)).

Further, it has been reported that the absorption of glyphosate(N-(phosphonomethyl)glycine, a non-selective herbicide) by plants is significantly facilitated when used in combination with Silwet L-77(Hanjung Chemicals, Inc., Korea), an organosilicon surfactant(Megh Singh, et al., *Proceedings of Fourth International Symposium on Adjuvants for Agrochemicals*, 385–390(1995)).

As described above, environmental and economic issues demand that the application rate of an agrochemical be kept at a minimal level, while maximizing the intended effectiveness thereof in protecting crops. This effectiveness depends on the amount of the agrochemical absorbed by the crops.

A general method for measuring the amount of agrochemicals absorbed by plants is based on the steps of applying a radiolabelled pesticide to a subject plant, washing the plant with a suitable solvent after a fixed time period, and measuring the radioactivity thereof. However, this method has problems of high cost and complexity which requires a special equipment and the attention of a specialist.

Accordingly, there exist no cost-effective methods for quantifying the foliar uptake of an agrochemical.

As to the procedure for screening penetrants which promote the uptake of an agrochemical by a subject crop, there have been reported the following two methods.

The first method comprises treating a subject plant with a mixture of a radiolabelled agrochemical and a penetrant candidate, and tracing the radio label. However, this method has the aforementioned problems of high cost and complexity.

The second method is based on the steps of applying a mixture of an agrochemical and a penetrant candidate to a subject plant and measuring directly the control effect of the agrochemical against weeds, pathogens or harmful insects. However, this method which requires cumbersome long experimental procedures yield only semi-quantitative data.

The present inventors have endeavored to develop a simple and accurate method for measuring the uptake rate of an agrochemical by a plant and a method for selecting a penetrant suitable for a given agrochemical and plant, and have discovered that a novel tracer can be advantageously employed in accomplishing the above objective.

SUMMARY OF THE INVENTION

Accordingly, it is an object of the present invention to provide a composition for quantifying the uptake of an agrochemical by a plant.

Another object of the present invention is to provide a method for quantifying the uptake of an agrochemical by a plant by employing said composition.

A further object of the present invention is to provide a method for selecting a penetrant by employing said method.

DETAILED DESCRIPTION OF THE INVENTION

In accordance with the present invention, there is provided a composition for measuring the foliar uptake of an agrochemical comprising the agrochemical and Congo Red as a tracer which is totally unabsorbable by plants.

Further, the present invention also provides a method for measuring the foliar uptake of an agrochemical comprising the steps of: (a) applying a composition containing said agrochemical and Congo Red to a plant and a control plate, (b) washing the plant and the control plate with a solvent to extract the agrochemical and Congo Red, (c) measuring the concentrations of the agrochemical and Congo Red in the wash extracts, and (d) calculating the foliar uptake of the agrochemical.

The method of the present invention can be applied for the selection of a suitable penetrant which enhances the uptake of a given agrochemical.

The present invention is described in more detail as follows.

A. Preparation of a Composition for Measuring the Foliar Uptake of an Agrochemical An agrochemical or a formulation thereof is dissolved, emulsified or suspended in water or a water-soluble solvent and Congo Red is added thereto as a tracer and mixed thoroughly to obtain the inventive composition for measuring the foliar uptake of the agrochemical. It is preferable to add Congo Red to the agrochemical solution at a lowest possible concentration, provided that it can be quantitatively analyzed by HPLC or spectrophotometry. For instance, Congo Red can be added to the agrochemical solution at a concentration ranging from 1 µg/ml to 1,000 µg/ml. If the concentration of Congo red in the agrochemical solution is higher than that of the agrochemical, penetration of the agrochemical into the plant may be inhibited, thereby biasing the uptake rate.

Exemplary agrochemicals that can be used in the present invention include all herbicides, insecticides, fungicides, plant growth regulators and the like known in the art.

In preparing the agrochemical solution, an available commercial formulation of agrochemical is merely diluted to a desired concentration by a conventional method. In case of a liquid or jelly-like agrochemical, it may be dissolved in a small amount of an organic solvent such as acetone, or dissolved or emulsified in water with the addition of a small amount of a surfactant, if necessary. In case of a solid agrochemical, it may be pulverized and mixed with a surfactant as a dispersing agent.

For the purpose of selecting a penetrant for a specific agrochemical, the inventive composition may further comprise a penetrant candidate material. The penetrant candidate material may be dissolved in water or an organic solvent and added to the inventive composition.

B. Application of the Inventive Composition to a Plant and to a Control Plate The inventive composition prepared as in section A above is then applied to a plant and to a control plate which does not absorb the agrochemical or the tracer.

Plant species that can be used in the present invention is not limited, but it is preferable to use a plant which is sufficiently matured and showing no sigh of aging.

The use of a control plate serves the purpose of determining the loss of agrochemical due to reasons other than plant uptake. The material of the control plate useful in the present invention is not limited as far as it neither absorbs, decomposes nor inactivates the inventive composition, and a glass plate is a preferred example thereof.

Congo Red is amenable to photodecomposition and, accordingly, all operations inclusive of the spraying of the agrochemical solution, and the storage and washing of the plants and the control plates are preferably carried out under a dim light, while avoiding direct sunlight. Generally, it is preferable to conduct the operations in a room under a fluorescent lighting.

When spraying the inventive composition to plants and control plates, it is preferable to use a spray booth for a uniform deposition of the composition to target surface. It is also preferable to spray a maximum amount of the composition, but not to the extent that the composition flows down the plants. For instance, the spraying amount of the composition may range from 1 to 100 l/ha for broad-leaf plants whose leaves are horizontal and large, e.g., cucumber and pepper, and from 50 to 300 l/ha for monocotyledonous plants whose leaves are erect and small in area, e.g., rice plants and barnyard grass. However, it should be understood that the spraying amount may vary according to the plant species and various other factors.

It is preferable to store the sprayed plants and control plates in a dark place.

C. Washing of the Composition

A selected number of the plants and control plates sprayed with the inventive composition as in section B are washed with a suitable solvent immediately after the spraying to obtain standard wash extracts that are used in defining base lines for the subsequent measurements. The remainder of the sprayed plants and control plates are kept in a dark place for a predetermined period and then subjected to similar washing to obtain wash extracts containing unabsorbed agrochemical and Congo Red. Suitable solvents for this wash extraction process include water, water-soluble organic solvents such as methanol, ethanol, acetone and acetonitrile, and a mixture thereof, wherein an acetonitrile-aqueous solution is preferred. When an aqueous solution of an organic solvent is used, the ratio of the water-soluble organic solvent to water may be varied from 0:10 (v/v) to 5:5(v/v) depending on the water-solubility of the agrochemical employed. Namely, it is preferable to lower the content of water-soluble organic solvent when the agrochemical has a high water-solubility, while a lower water content is preferable when the agrochemical has a low water-solubility.

In washing the sprayed plants, an exposed part of the plant is cut and put in a test tube containing a suitable washing solution, and the test tube is capped and agitated with bottom-side up at 50 to 80 rpm for 1 to 5 minutes. The sprayed control plates may be put in a petri dish having a suitable size and washed with the same solvent as above.

D. Measuring the Concentrations of Agrochemical and Congo Red and Calculation of the Uptake Rate The concentrations of the agrochemical and Congo Red in the wash extracts obtained in section C are measured by conventional methods, e.g., HPLC, gas chromatography and spectrophotometry.

Subsequently, the foliar uptake of the agrochemical is calculated by the steps of:

(1) calculating the respective concentration ratios of the agrochemical and Congo Red(Conc. of agrochemical/Conc. of Congo Red) for the initial wash extracts of the plant and control plate obtained immediately after the spraying;

(2) calculating the respective concentration ratios of the agrochemical and Congo Red(Conc. of the agrochemical/Conc. of Congo Red) for the wash extracts of the plant and control plate obtained at a predetermined time after the spraying;

(3) dividing the concentration ratio of the agrochemical and Congo Red calculated in (2) by that calculated in (1) for the wash extracts of the plant and control plate, respectively, to obtain the ratio of the agrochemical remaining on the surface of the plant and control plate at the predetermined time after the spraying;

(4) subtracting the ratio of the agrochemical remaining on the surface of the plant from that of the control plate to obtain the fraction the agrochemical absorbed by the plant.

The inventive method for measuring the uptake rate of an agrochemical will be understood more easily with the following exemplary case.

An agrochemical solution comprising 100 ppm of an agrochemical and 100 ppm of Congo Red is prepared and sprayed to two cucumber leaves and two glass plates. Immediately after the spraying, one cucumber leaf and one glass plate are washed with 10 ml of a solvent, respectively, and the concentrations of the agrochemical and Congo Red in the wash extracts are measured by HPLC. On the other hand, the remaining cucumber leaf and glass plate are stored in a dark room for 24 hours and, then, washed with 10 ml of the same solvent. The concentrations of the agrochemical and Congo Red in the wash extracts are also measured by HPLC. The uptake of the agrochemical by cucumber leaves is calculated according to the previously described procedure, as in Table 1.

TABLE 1

| Sample | Time | Measured Conc. (ppm) Congo Red | Measured Conc. (ppm) Agro-chemical | Calculated Conc. of agrochemical/ Conc. of Congo Red | Calculated Ratio of agrochemical remaining on the surface | Uptake of agrochemical |
|---|---|---|---|---|---|---|
| Cucumber leaf | I.A.* | 1.000 | 0.999 | 1.001 | 0.812 | 0.118 |
|  | after 24 h | 0.800 | 0.650 | 0.813 |  |  |
| Glass plate | I.A.* | 1.500 | 1.498 | 0.999 | 0.930 |  |
|  | after 24 h | 1.400 | 1.300 | 0.929 |  |  |

*I.A.: Immediately after the spraying

As discussed above, Congo Red is neither absorbable by plants nor volatilizable. Accordingly, the total amount of the agrochemical lost due to the absorption by a plant and other factors such as evaporation and decomposition can be calculated by comparing the amounts of the agrochemical and Congo Red found on the plant immediately after the spraying and at predetermined time after the spraying of inventive composition. Further, as a glass plate absorbs no material, the ratio of the agrochemical remaining on the glass plate reflects the ratio of the agrochemical lost by reasons other than absorption by the plant. Accordingly, an accurate figure for the foliar uptake of the agrochemical can be easily calculated by comparing the ratios of the agrochemical remaining on the plant and the glass plate.

As previously discussed, the method of the present invention employing Congo Red as a tracer for an agrochemical is useful for accurate assessment of the amount of the agrochemical absorbed by a plant. Further, the inventive method is also useful for the selection of a penetrant suitable for a specific agrochemical and plant. The present invention can be advantageously used in determining the lowest effective application rates of various agrochemicals, thereby creating benefits in terms of both economy and protection of the environment.

The following Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

EXAMPLE 1

Uptake Rates of Various Agrochemicals by Cucumber Plants (Step 1) Preparation of a solution containing agrochemicals and Congo Red Measured amounts of procymidone wettable powder(50% ai, Dongbang Agro Corporation, Korea), fenarimol emulsifiable concentrate(12.5% ai, Oriental Chemical Industries, Korea) and dimethomorph wettable powder(25% ai, Dongbang Agro Corporation, Korea) were placed in an Erlenmeyer flask, and water and an aqueous Congo Red solution were added thereto to final concentrations of 500 ppm, 31.25 ppm and 250 ppm, respectively, while adjusting the Congo Red concentration to 400 ppm. Since dimethomorph is not readily absorbed by the plant, 0.1% of stearylamine ethoxylate(SN, moles of ethylene oxide added: 10) was added as an adjuvant to enhance its foliar uptake.

(Step 2) Spraying of the agrochemical solution

Cucumber seeds(Baktadagi, Hung Nong Seed Co., Ltd., Korea) were sowed in disposable resin cup pots (id 47 mm×50 mm) at a density of three seeds per pot and cultivated in a greenhouse. Upon the complete development of cotyledons, the cucumber plants were each transplanted to a disposable resin cup pot(id 66 mm×h 66 mm) and cultivated in a greenhouse until the development of 4 to 5 leaves.

18 pots of cucumber plants thus prepared were put in a spray booth and sprayed with the agrochemical solution prepared in (Step 1) in an amount of 80 l/ha. Further, 15 glass plates(10 cm×10 cm) were also sprayed with the same agrochemical solution prepared in (Step 1) in an amount of 80 l /ha.

(Step 3) Washing of the cucumber leaves and the glass plates

Prepared as washing solutions were 20 ml of 40% acetonitrile-aqueous solution for procymidone and two 20 ml portions of 30% acetonitrile-aqueous solution for fenarimol and dimethomorph, which were placed in test tubes(id 32 mm×h 200 mm) and capped.

Immediately after the spraying in (Step 2), one leaf with its petiole attached was cut off from each of three cucumber plants, put in a test tube containing the appropriate washing solution and washed by agitating the tube with bottom-side up at 60 to 70 rpm for 2 minutes to obtain three wash extracts. Three glass plates were subjected to the same washing procedure in a petri dish(id 15.2 cm) to obtain three control wash extracts.

The remaining 15 cucumber plants and 12 glass plates were stored in the dark at room temperature, and the same washing procedure as above was repeated at 1 hour, 3 hours, 6 hours, 12 hours and 24 hours after the spraying.

(Step 4) Quantification of the agrochemicals and Congo Red and calculation of the uptake rate The concentrations of the agrochemicals in the wash extracts were measured by HPLC(Spectra 200 Programmable Wavelength Detector, acetonitrile-water solvent programming, 42%–80%). The wash extracts obtained immediately after the spraying were used as standard solutions, and Congo Red, as an internal standard. The foliar uptake rate of each of the agrochemicals was calculated based on the amount of the agrochemical found on the glass plate control and that on the cucumber leaves.

The result is shown in Table 2.

TABLE 2

| | Time-dependent Uptake by Cucumber(%) (Mean ± S.D.(n = 3)) | | | | | | Formulation of the agrochemical |
|---|---|---|---|---|---|---|---|
| | I.A.* | after 1 hr | after 3 hrs | after 6 hrs | after 12 hrs | after 24 hrs | |
| Procymidone | 0 ± 0.8 | 1.9 ± 1.4 | 3.7 ± 3.3 | — | 4.1 ± 0.2 | 5.7 ± 1.0 | Wettable powder |
| Fenarimol | 0 ± 3.1 | 2.0 ± 8.1 | 3.2 ± 1.8 | 5.2 ± 2.5 | 8.0 ± 4.1 | 15.1 ± 4.0 | Emulsifiable concentrate |
| Dimethomorph | 0 ± 0.7 | 5.4 ± 2.2 | 12.5 ± 2.0 | 19.2 ± 2.4 | 21.3 ± 1.7 | 22.7 ± 3.6 | Wettable powder |

*I.A.: Immediately after the spraying

As shown in Table 2, only 5.7% of procymidone, a horticultural fungicide, was absorbed by the cucumber leaves at 24 hours after its spraying.

Nobuyoshi Mikami et al. have reported that 73.2% of procymidone applied to cucumber leaves in a greenhouse was recovered after 8 days since its application(J. Pesticide Sci., 9, 131–136(1984)). However, this result reflects every possible causes of loss on the surface of the leaves. It is assumed that the actual uptake rate by the cucumber leaves after 24 hours since the application of procymidone would not more than the present finding. Accordingly, this result is more or less consistent with the present finding.

In the meantime, there was observed a continuously increasing amount of absorbed fenarimol ranging from 0(immediately after the spraying) to 15.1% (at 24 hours after the spraying). This result is also consistent with the findings of Peter, J. G. et al. (Pestic. Sci., 24, 31–53(1988)), who have reported that, in an experiment using four species of plant, the uptake rate of fenarimol varies widely from 1.4% to 11.4% when an adjuvant was not added.

In case of dimethomorph, more than 20% thereof was absorbed at 24 hours after the spraying the solution which contained 0.1% SN as a penetrant.

These results demonstrates the usefulness of the present method in measuring foliar uptake rates of agrochemicals.

EXAMPLE 2

Uptake Rates of Various Agrochemicals by Rice Plants (Step 1) Preparation of a solution containing agrochemicals and Congo Red Measured amounts of edifenphos(30% emulsifiable concentrate, Misung Co., Ltd., Korea), isoprothiolane(40% emulsifiable concentrate, Hankook Samgong Co., Ltd., Korea) and tricyclazole(75% wettable powder, Chunjin Co., Ltd., Korea) were placed in an Erlenmeyer flask, and water and an aqueous Congo Red solution were added thereto to final concentrations of 600 ppm, 800 ppm and 300 ppm, respectively, while adjusting the Congo Red concentration to 400 ppm.

(Step 2) Spraying of the agrochemical solution

Rice seeds(rice cultivar, Dongjin byeo) were sowed in seedbeds and cultivated in a greenhouse. Rice plants at the three-leaf stage were transplanted to disposable resin cup pots(id 66 mm×h 66 mm) at a density of three plants per pot and cultivated in a greenhouse until they reached the four-leaf stage of tillers, followed by removing aged leaves.

Twelve rice pots thus prepared were put in a spray booth and sprayed with the agrochemical solution prepared in (Step 1) in an amount of 250 l/ha. Further, 12 glass plates(10 cm×10 cm) were also sprayed with the same agrochemical solution in an amount of 125 l/ha.

(Step 3) Washing of the rice plants and the glass plates

Thirty percents of acetonitrile-aqueous solution was prepared as a washing solution and 20 ml portions thereof were placed in test tubes(id 32 mm×h 200 mm) and capped.

Immediately after the spraying in (Step 2), the exposed parts of the rice plants of two rice pots were harvested and put in two of the test tubes containing the washing solution and washed by agitating the tubes with bottom-side up at 60 to 70 rpm for 2 minutes to obtain standard wash extracts. Two glass plates were respectively put in a petri dish(id 15.2 cm) and washed with a 20 ml portion of the same washing solution as above to obtain standard controls.

The remaining 10 rice pots and 10 glass plates were stored in the dark at room temperature, and the same washing procedure as above was repeated at 1 hour, 3 hours, 6 hours, 12 hours and 24 hours after the spraying to obtain five time-dependent wash extracts as well as controls.

(Step 4) Quantification of the agrochemicals and Congo Red and calculation of the uptake rate The concentrations of edifenphos and isoprothiolane in the wash extracts were measured by HPLC(Spectra 200 Programmable Wavelength Detector, acetonitrile-water solvent programming, 30%–80%). The wash extracts obtained immediately after the spraying were used as standard extracts, and Congo Red, as an internal standard. The tricyclazole concentration was measured by HPLC, while Congo Red was quantified with a spectrophotometer (SHIMADZU, Model UV-2401PC UV-VIS Recording Spectrophotometer, 497 nm).

The foliar uptake rates of the agrochemicals were calculated based on the amounts of the agrochemicals found on the glass plates and the rice leaves.

The result is shown in Table 3.

TABLE 3

| | Time-dependent Uptake by Rice(%) (Mean ± S.D.(n = 3)) | | | | | | Formulation |
|---|---|---|---|---|---|---|---|
| | I.A.* | after 1 hr | after 3 hrs | after 6 hrs | after 12 hrs | after 24 hrs | of the agrochemical |
| Edifenphos | 0 ± 1.3 | 1.5 ± 1.1 | 4.9 ± 0.7 | 7.8 ± 0.4 | 14.5 ± 1.3 | 29.8 ± 1.9 | Emulsifiable concentrate |
| Isoprothiolane | 0 ± 1.0 | 7.9 ± 1.9 | 11.6 ± 1.2 | 16.1 ± 1.3 | 27.8 ± 1.1 | 47.1 ± 2.5 | Emulsifiable concentrate |
| Tricyclazole | 0 ± 1.1 | 1.4 ± 0.7 | 1.1 ± 1.5 | 2.0 ± 1.4 | 4.1 ± 0.5 | 11.0 ± 0.9 | Wettable powder |

*I.A.: Immediately after the spraying

As shown in Table 3, edifenphos, isoprothiolane and tricyclazole, which are agrochemicals for controlling rice blast, are absorbed by the rice plants at a steady rate. These findings support that those agrochemicals have good systemicities.

EXAMPLE 3

Selection of a Penetrant for the Absorption of Dimethomorph by Cucumber Leaves Forum wettable powder(a 25% dimethomorph formulation, Dongbang Agro Co., Ltd., Korea) was dispersed in water and added thereto were one of the penetrant candidate materials listed in Table 4 and Congo Red to obtain an agrochemical solution containing dimethomorph, a penetrant candidate and Congo Red at concentrations of 250 ppm, 1,000 ppm and 200 ppm, respectively. A control containing no penetrant was also prepared.

The agrochemical solution and control thus prepared were sprayed on leaves of each of six cucumber plants having 4 to 5 leaves, as well as on six glass plates(10 cm×10 cm). Immediately after the spraying, the sprayed cucumber leaves from 3 cucumber plants and three glass plates were washed with 12 ml portion of 30% acetonitrile-aqueous solution for 3 minutes to obtain standard wash extracts and controls.

The remaining three cucumber pots and three glass plates were stored in the dark at room temperature, and the same procedure was repeated at 24 hours after the spraying.

The above series of experiments were repeated for each of the penetrant candidates shown in Table 4.

The concentrations of dimethomorph and Congo Red in the wash extracts were measured by HPLC(Spectra 200 Programmable Wavelength Detector, acetonitrile-water solvent programming, 42%–80%). The wash extracts obtained immediately after the spraying were used as standard solutions, and Congo Red, as an internal standard. The foliar uptake rate of dimethomorph was calculated by comparing the concentrations of dimethomorph and Congo Red in the wash extracts obtained immediately after the spraying and at 24 hours after the spraying.

The result is shown in Table 4.

TABLE 4

| Penetrants (Moles of ethylene oxide added) | Recovery (%) | Uptake (%) |
|---|---|---|
| nonylphenol ethoxylate(10) | 99.8 | 0.2 |
| tridecyl alcohol ethoxylate(5) | 98.0 | 2.0 |
| laurylamine ethoxylate(7) | 96.3 | 3.7 |

TABLE 4-continued

| Penetrants (Moles of ethylene oxide added) | Recovery (%) | Uptake (%) |
|---|---|---|
| stearylamine ethoxylate(10) | 85.5 | 14.5 |
| castor oil ethoxylate(17) | 94.9 | 5.1 |
| sodium dioctylsulfosuccinate | 94.5 | 5.5 |
| N-Octylpyrrolidone | 98.1 | 1.9 |
| Silwet L-77 | 100.0 | 0.0 |
| None (Control) | 99.7 | 0.3 |
| Glass plate | 100.0 | 0.0 |

As shown in Table 4, nearly 100% of the initial amount of dimethomorph was recovered in case of the control and the glass plate after 24 hours since the spraying, showing that dimethomorph was not absorbed by the cucumber leaves nor lost by any other factors. However, the experimental groups employing the indicated penetrants showed various absorption rates, and it was determined that suitable penetrants for promoting the absorption of dimethomorph by cucumber plants are stearylamine ethoxylate, sodium dioctylsulfosuccinate and castor oil ethoxylate.

EXAMPLE 4

Selection of a Penetrant for Promoting Tricyclazole Absorption by Rice Plants Beam wettable powder(a 75% tricyclazole formulation, Oriental Chemical Industries, Korea) was suspended in water and added thereto were one of the penetrant candidates listed in Table 5 and Congo Red to obtain an agrochemical solution containing tricyclazole, a penetrant candidate material and Congo Red at concentrations of 400 ppm, 1,000 ppm and 400 ppm, respectively. A control containing no penetrant was also prepared.

The agrochemical solution and control thus prepared were sprayed on six rice pots containing 4-leaf stage rice tillers as well as on six glass plates (10 cm×10 cm). Immediately after the spraying, the rice plants of three rice pots and three glass plates were washed with 20 ml portion of 30% acetonitrile-aqueous solution for 3 minutes to obtain standard wash extracts.

The remaining 3 rice pots and 3 glass plates were stored in the dark at room temperature, and the same washing procedure was repeated at 24 hours after the spraying.

The above series of experiments were repeated for each of the penetrant candidates shown in Table 5.

The concentrations of Congo Red in the wash extracts were measured with a spectrophotometer(SHIMADZU, Model UV-2401PC UV-VIS Recording Spectrophotometer, 497 nm) and those of tricyclazole in the wash extracts were measured by HPLC(Spectra 200 Programmable Wavelength Detector, acetonitrile-water solvent programming, 30%–80%). The wash extracts obtained immediately after the spraying were used as standard solutions, and Congo Red, as an internal standard. The foliar uptake of tricyclazole was calculated by comparing the concentrations of tricyclazole and Congo Red in the wash extracts obtained immediately after the spraying and at 24 hours after the spraying.

The result is shown in Table 5.

TABLE 5

| Penetrants (Moles of ethylene oxide added) | Recovery (%) | Uptake (%) |
|---|---|---|
| nonylphenol ethoxylate(10) | 80.6 | 19.4 |
| lauryl alcohol ethoxylate(5) | 68.7 | 31.3 |
| tridecyl alcohol ethoxylate(5) | 75.6 | 24.4 |
| laurylamine ethoxylate(7) | 35.4 | 64.6 |
| stearylamine ethoxylate(10) | 46.1 | 53.9 |
| castor oil ethoxylate(17) | 63.7 | 36.3 |
| sodium dioctylsulfosuccinate | 79.1 | 20.9 |
| Silwet L-77 | 72.3 | 27.7 |
| None (Control) | 82.4 | 17.6 |
| Glass plate | 99.8 | 0.2 |

As shown in Table 5, nearly 1000 of the initial amount of tricyclazole was recovered in the glass plate run after 24 hours since the spraying, showing that tricyclazole is stable, and it is lost only by absorption by rice plants as in the control run wherein an uptake of 17.6% took place in the 24 hour period. The experimental groups employing the indicated penetrants showed higher absorption rates, and it was determined that suitable penetrants for promoting the absorption of tricyclazole by rice plants are laurylamine ethoxylate, stearylamine ethoxylate and lauryl alcohol ethoxylate.

TEST EXAMPLE 1

Controlling of Downy Mildew(*Pseudopernospora cubensis*) in Cucumber by Employing Forum Wettable Powder Cucumber leaves infected with *Pseudopernospora cubensis* in a greenhouse were gathered, and stored in a humid chamber for 1 day to allow the spore formation, followed by collecting the spores using sterilized water. The spore suspension thus obtained was examined under a hematocytometer and the concentration of spores was adjusted to $5 \times 10^3$ sporangia/ml. This spore suspension was sprayed on 3-leaf stage cucumber plants grown in a glasshouse. The cucumber plants were stored in a humid chamber having a relative humidity of more than 950- at 25° C. for 17 to 20 hours and then allowed to dry at room temperature for 2 to 3 hours.

Forum wettable powder was suspended in water and added thereto was stearylamine ethoxylate(SN, moles of ethylene oxide added: 10) to prepare an agrochemical solution containing Forum wettable powder and SN at concentrations of 125 μg/ml and 1,000 μg/ml, respectively. The agrochemical solution was further diluted with water to obtain 2- and 4-fold diluted spray solutions. A control containing only Forum wettable powder was also prepared. The agrochemical solutions were then sprayed on the cucumber plants prepared as above. The treated cucumber plants were stored in a room maintained at 26° C. and a relative humidity of 80 to induce infection by *Pseudopernospora cubensis*. Then, the fractional coverage of spotted area on leaves was visually assessed. The above experiments were conducted with 5 replications and the curative activity (W) was calculated by the following equation.

$$\text{Curative activity (\%)} = \frac{\begin{array}{c}\text{Fractional coverage}\\\text{of spotted area}\\\text{in non-treated group}\end{array} - \begin{array}{c}\text{Fractional coverage}\\\text{of spotted area}\\\text{in treated group}\end{array}}{\text{Fractional coverage of spotted}\text{ area in non-treated group}} \times 100$$

The result is shown in Table 6.

TABLE 6

| | | Curative activity (%) | |
|---|---|---|---|
| | | Wettable powder | Wettable powder + SN |
| Conc. of dimethomorph (μg/ml) | 31 | 11 | 0 |
| | 63 | 0 | 11 |
| | 125 | 11 | 86 |
| 50% antifungal conc. (calculated) | | ≧125 μg/ml | 83 μg/ml |

As shown in Table 6, the agrochemical solution comprising the Forum wettable powder together with stearylamine ethoxylate exhibited significantly higher curative activity against *Pseudopernospora cubensis* than the Forum wettable powder itself.

While the invention has been described with respect to the above specific embodiments, it should be recognized that various modifications and changes may be made to the invention by those skilled in the art which also fall within the scope of the invention as defined by the appended claims.

What is claimed is:

1. A composition for measuring the foliar uptake of an agrochemical selected from the group consisting of herbicides, insecticides, fungicides and plant growth regulators which comprises said agrochemical and an inert tracer consisting of Congo Red.

2. A method for measuring the foliar uptake of an agrochemical selected from the group consisting of herbicides, insecticides, fungicides and plant growth regulators comprising the steps of:

(a) applying a composition containing said agrochemical and an inert tracer consisting of Congo Red to a plant and a control plate, (b) washing the plant and the control plate with a solvent to extract the agrochemical and the inert tracer, (c) measuring the concentrations of the agrochemical and the inert tracer in the wash extracts, and (d) calculating the foliar uptake of the agrochemical.

3. The method of claim 2, wherein the solvent is selected from the group consisting of water, methanol, ethanol, acetone, acetonitrile and a mixtures thereof.

4. The method of claim 2, wherein the composition containing the agrochemical and the inert tracer in Step (a) further contains a penetrant candidate for the purpose of selecting a penetrant suitable for the agrochemical.

5. The method of claim 2, wherein the composition containing the agrochemical and Congo Red in Step (a) further contains a penetrant.

6. A composition comprising an agrochemical selected from the group of herbicides, insecticides, fungicides and plant growth regulators and an inert tracer consisting of Congo Red.

7. The composition of claim 6 where the agrochemical is an herbicide.

8. The composition of claim 6 where the agrochemical is an insecticide.

9. The composition of claim 6 where the agrochemical is a fungicide.

10. The composition of claim 6 where the agrochemical is a plant growth regulator.

* * * * *